United States Patent [19]

Meyer et al.

[11] 4,446,577

[45] May 8, 1984

[54] ARTIFICIAL HEART VALVE

[75] Inventors: Louis C. Meyer, Denver, Colo.; Samuel H. Goodenough, Dana Point, Calif.

[73] Assignee: Mitral Medical International, Inc., Wheat Ridge, Colo.

[21] Appl. No.: 213,944

[22] Filed: Dec. 8, 1980

Related U.S. Application Data

[63] Continuation-in-part of Ser. No. 144,034, Apr. 28, 1980, abandoned.

[51] Int. Cl.³ .............................................. A61F 1/22
[52] U.S. Cl. ............................................................ 3/1.5
[58] Field of Search .............................................. 3/1.5

[56] References Cited

U.S. PATENT DOCUMENTS

| 3,312,237 | 4/1967 | Mon et al. | 137/512.15 |
|---|---|---|---|
| 3,445,863 | 5/1969 | Wada | 3/1 |
| 3,589,392 | 6/1971 | Meyer | 137/525.1 |
| 3,737,919 | 6/1973 | Child | 3/1 |
| 3,903,548 | 11/1975 | Nakib | 3/1.5 |
| 4,011,601 | 3/1977 | Clune et al. | 3/1.5 |
| 4,159,543 | 7/1979 | Carpentier | 3/1.5 |
| 4,178,639 | 12/1979 | Bokros | 3/1.5 |
| 4,240,161 | 12/1980 | Huffstutler, Jr. et al. | 3/1.5 |
| 4,254,508 | 3/1981 | Bokros | 3/1.5 |
| 4,272,854 | 6/1981 | Bokros | 3/1.5 |
| 4,276,658 | 7/1981 | Hanson et al. | 3/1.5 |
| 4,308,624 | 1/1982 | Klawitter | 3/1.5 |
| 4,326,304 | 4/1982 | Klawitter | 3/1.5 |
| 4,328,592 | 5/1982 | Klawitter | 3/1.5 |
| 4,357,715 | 11/1982 | Klawitter | 3/1.5 |

Primary Examiner—Clifford D. Crowder
Attorney, Agent, or Firm—John E. Reilly

[57] ABSTRACT

A prosthetic heart valve has at least one occluder leaflet in which lateral extensions on each leaflet are insertable into generally trapezoidal or triangular depressions formed in diametrically opposed extension walls of the valve body and which depressions both guide and limit the opening and closing movement of each leaflet through predetermined angles of movement.

23 Claims, 21 Drawing Figures

_FIG_ 11

_FIG_ 12

_FIG_ 14

_FIG_ 13

ARTIFICIAL HEART VALVE

This application is a continuation-in-part of Ser. No. 144,034, now abandoned, for ARTIFICIAL HEART VALVE, filed Apr. 28, 1980 by Louis C. Meyer and Samuel H. Goodenough, and assigned to the assignee of the present application.

This invention relates to valves and more particularly relates to artificial heart valves which can be transplanted into the mitral, aortic, tricuspid or pulmonic portions of the heart.

FIELD OF THE INVENTION

Numerous types of prosthetic heart valves have been devised to the end of replacing defective natural heart valves and to simulate as closely as possible the operation of natural heart valves. Essentially, the natural valves in the human heart operate as check valves which are capable of operating between open and closed positions in response to the flow of blood to and from the heart. As disclosed in prior copending application for patent, Ser. No. 84,318, filed Oct. 12, 1979, now U.S. Pat. No. 4,363,142 and assigned to the assignee of this application, it is essential that the artificial heart valve be capable of achieving the rapid response time of the natural heart valve to the reverse flow of blood in moving between the open and closed positions. Moreover, the valve should be capable of achieving a maximum opening to an angle in excess of 60° to the transverse axis of the valve for the passage of blood with a minimum of turbulence. Further, the valve must have a low profile or height so as to prevent any possible interference with the ventricular septum as well as to minimize aortic obstruction and low cardiac output. In this same relation, it is equally important that there be a low pressure gradient between the upstream and downstream ends of the valve when the valve is in its open position. For instance, a pressure gradient on the order of 20 millimeters to 50 millimeters of mercury in a natural heart valve is symptomatic of defective functioning of the valve; whereas, the pressure gradient or drop of a properly functioning valve should be less than 10 millimeters of mercury.

Previously, U.S. Letters Pat. No. 3,589,392 employed curved leaflets which were hinged to a valve body for pivotal movement between the open and closed positions. More recently, the hereinbefore referred to copending application for patent was directed to a novel and improved form of guide assembly which is especially adapted for curved leaflets so as to directionally control the movement of the leaflets in response to the direction of liquid or blood flow therethrough, the guide assembly including guide channels in the wall of the valve body which receive lateral projections on opposite sides of the leaflets. The guide channels take the form of generally polygonal shaped pockets, and the lateral projections are defined by elongated members which are dimensioned to slide as well as pivot through the channels in regulating the opening and closing of the leaflets. In that approach, the lateral projections are mounted on flat skirts so as to enhance the response time of the leaflets.

Others have proposed leaflet-type valves which are capable of pivotal or swinging movement about a fixed axis, such as, by pins or notched elements serving as lateral projections which are insertable into sockets in the wall of the body. Representative of this approach are disclosed in U.S. Letters Pat. Nos. 3,626,518 and 3,312,327. Further, U.S. Letters Pat. Nos. 4,011,601 and 3,903,548 disclose the use of depressions or guide surfaces which will minimize possible deleterious effects of sockets permitting blood to clot or accumulate in or around any relatively sharp edges of the sockets and prevent effective washing action by the blood. It has also been proposed in the past to form an axially directed extension of the valve body in which guide surfaces are mounted for the purpose of establishing the pivot point or axis for swinging movement of the leaflets between the open and closed position without substantially increasing the profile or height of the valve. For example, reference is made to U.S. Letters Pat. No. 4,178,639. In that patent however separate stops are required to regulate the limits of movement of the leaflets, and the leaflets are positioned substantially in the central region of blood flow through the valve when in the open position.

SUMMARY OF THE INVENTION

It is therefore an object of the present invention to provide for a novel and improved artificial heart valve in which one or more valving elements are movable between an open and closed position in response to the direction of fluid flow therethrough with a minimum of wear and stress imposed upon the elements of the valve.

Another object of the present invention is to provide for a novel and improved prosthetic heart valve in which one or more leaflets or valve elements are movable through a minimum angle between a fully closed and a fully opened position; and in the open position the leaflet or leaflets will permit substantially unrestricted flow of blood therethrough so as to minimize turbulence and promote laminar flow of the blood.

It is another object of the present invention to provide for a prosthetic heart valve in which one or more valve members are so mounted and arranged as to avoid collection of blood at or along the pivot points or axes for each valve while eliminating any sharp projections or stops protruding into the passageway of each valve.

A further object of the present invention is to provide a prosthetic heart valve of the leaflet type in which one or more leaflet elements are so constructed and arranged as to increase the effective orifice area or passageway through the valve with a minimal pressure gradient thereacross; further to reduce the thickness and size of the valve body and avoid necessity for a fixed point of rotation at the juncture between each leaflet and valve body which cannot be effectively washed by the flow of blood.

It is an additional object of the present invention to provide for a low profile valve body for a prosthetic heart valve in which guide extensions on the body serve the dual function of guiding and limiting movement of a leaflet while avoiding localized wear and which further obviate the use of fixed pivots or hinges; and, in general, the valve constructions devised will promote long wear, durability, quiet operation with rapid response time while employing a minimum number of parts and greatly simplifying the manufacture of the valve.

It is a still further object of the present invention to provide in a low profile valve body for a novel and improved leaflet having guide elements cooperating with recessed guide extensions in the body to establish optimum contact therebetween as the valve undergoes opening and closing movement; and further wherein the leaflet is capable of advancing to a precisely controlled open position without the use of separate stop elements with improved flow along the minor orifice of the valve in the open position and precisely controlled leakage in the closed position.

The preferred embodiment of the present invention resides in the formation of a low profile, prosthetic heart valve in which axially directed extensions on diametrically opposed sides of the valve body are provided with shallow guide channels which are adapted to receive gently curving, lateral projections on an occluder leaflet so as to control pivotal movement of the leaflet between open and closed positions in response to the direction of blood flow therethrough. The spacing and configuration of the guide channels are such that they are capable of guiding the leaflet in its movement between the open and closed positions as well as controlling its extreme limits of movement; yet the channels are so configured as to avoid formation of any sharp edges or fixed points of rotation for the lateral projections in their movement through the channels. Preferably, the foregoing is achieved by forming the guide channels of generally trapezoidal configuration with opposed sidewalls diverging in a downstream direction through axially directed extensions of the valve body, the inner wall or bearing surface of each guide channel being of generally curvilinear configuration. Preferred and alternate forms of the invention are presented herein either for a mono-leaflet, bi-leaflet or tri-leaflet valve, respectively, in which the leaflets are arranged to move in a radially outward direction away from the center line of the valve into the open position, as opposed to moving toward the center of the valve in the open position. In the mono-leaflet valve, the leaflet is supported in the closed position on a ledge of the valve body. The upstream side of the occluder leaflet is of a gently curved convex shape and the downstream side is a concave curve. This provides a significant increase in the flow area between the open occluder leaflet and the valve body on the side proximal to the projections and guide channels, otherwise referred to as the "minor orifice", when the leaflet is in the open position.

In the single leaflet construction, an optimum curvature is established for the guide members on the leaflet so that in their placement within and movement through the guide channels an optimum contact angle is established which will assure movement between precisely defined angles in the open and closed position notwithstanding the ability of the guide members to undergo translatory movement in combination with their pivotal movement through the guide channels.

The above and other objects, advantages and features of the present invention will become more readily understood and appreciated from a consideration of the following detailed description of a preferred embodiment of the present invention when taken together with the accompanying drawings in which:

DESCRIPTION OF THE PREFERRED BI-LEAFLET EMBODIMENT

In the preferred form of present invention, as illustrated in FIGS. 1 to 7, a bi-leaflet valve 10 is comprised of a valve body 12 of generally annular configuration having diametrically opposed arcuate wall sections 13 interconnected by straight wall sections 14, and the valve body is surrounded by an outer concentric suture ring 15. Valve members or occluder leaflets 16 are disposed for pivotal movement within the valve body in a manner to be hereinafter described in more detail.

Figure 2:
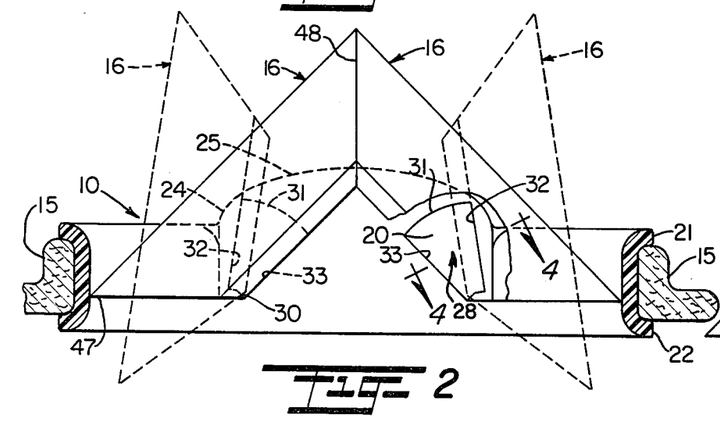
FIG. 2 is a cross-sectional view taken about lines 2—2 of FIG. 1.
Figure 3:
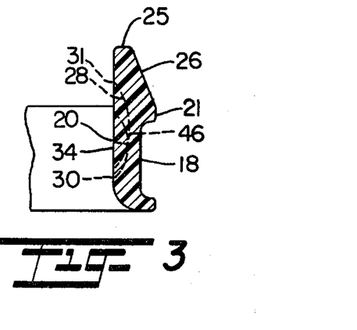
FIG. 3 is a cross-sectional view taken about lines 3—3 of FIG. 1.

Both the arcuate wall sections 13 and the straight wall sections 14 are of generally channel-shaped cross-sectional configuration, as noted from the cross-sectional views of FIGS. 2 and 3, so as to define a generally concave, channel-shaped external wall surface 18 which is adapted to receive the suture ring 15, the suture ring being of conventional construction and provided with an outwardly projecting collar 18 to facilitate implantation of the valve into the heart, for instance, as a substitute for the mitral valve. A modified type of suture ring, not shown, may be employed when the valve is to be implanted in place of the aortic valve.

An inner wall surface 20 of the valve body 12 is characterized by being flat throughout its greater height except for the downstream and upstream ends 21 and 22 which flare outwardly to form the external channel-shaped configuration of the external wall 18. In addition, each straight wall section 14 is provided with an axial extension 24, each extension forming a direct continuation of the inner wall surface 20 in a downstream direction and terminating in a somewhat convex downstream edge 25. Each extension 24 is symmetrically formed about the center of its associated straight wall section and has an external inclined wall surface 26 which converges upwardly from the upper end 21 into the convex edge 25 of the extension.

Figures 4, 7:
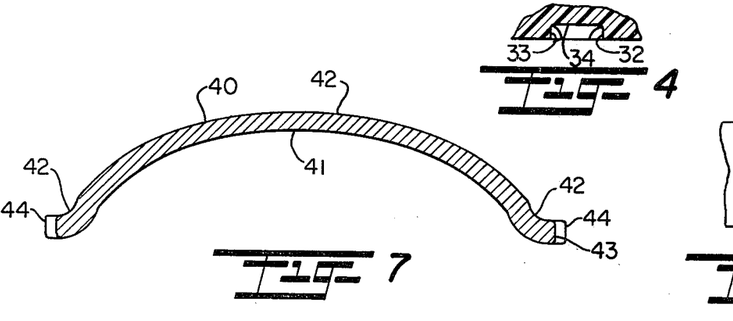
FIG. 4 is a view taken about lines 4—4 of FIG. 2.
FIG. 7 is a cross-sectional view taken about lines 7—7 of FIG. 5.

A pair of guide pockets in the form of shallow recesses or channels 28 are formed at opposite ends of each straight wall section 14 and as illustrated in FIGS. 2 to 4, each channel is of a height to project from a point adjacent to upstream or lower edge 22 of the wall section to the downstream or convex edge 25 of the extension wall 24. As viewed in FIG. 2, each guide pocket or channel 28 is of generally triangular configuration which is truncated by the intersection of a relatively short upstream edge 30 with divergent side edges 32 and 33. The upstream edge 30 is of a width just greater than the width of the guide member to be described for the associated leaflet, and a relatively wide downstream edge 31 is of curved or arcuate configuration. In the preferred form, the divergent edge 32 is disposed at an angle on the order of 5° to 9° to the longitudinal axis of the valve while the edge 33 which establishes the closed position of the valve, is disposed at an angle on the order of 45° to the longitudinal axis. The inner wall or bearing surface 34 of each channel is of somewhat curvilinear configuration having an arcuate or somewhat elliptical intermediate wall surface which verges into sloping or gently curving surfaces at the outer surrounding edges 30 and 31, as shown in FIG. 3, but is flat across its width and terminates in the more sharply angled edges 32 and 33, as shown in FIG. 4.

Figure 1:
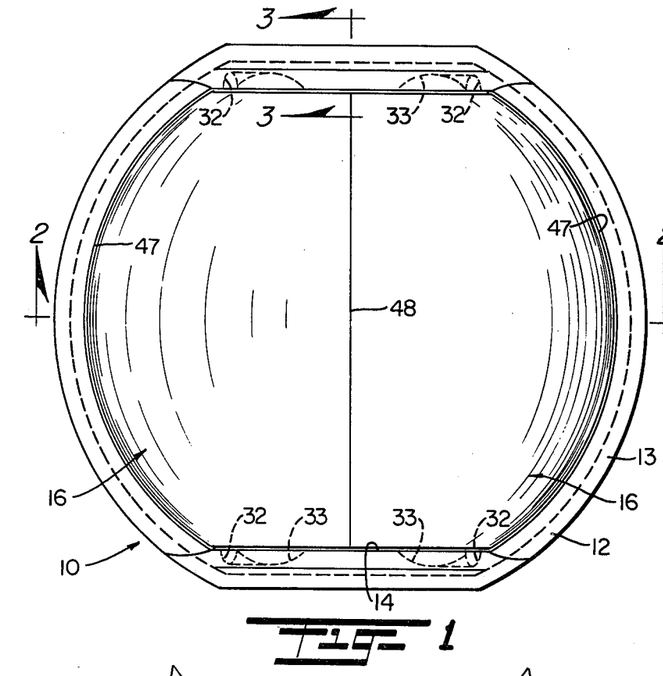
FIG. 1 is a plan view of a preferred form of bi-leaflet artificial heart valve as viewed from the downstream side of the valve, in accordance with the present invention.

The occluder leaflets 16 are mounted for pivotal movement within the channel 28 between a closed position as illustrated in full in FIGS. 1 and 2 and an open position as shown dotted in FIG. 2. The leaflets 16 are of corresponding size and configuration and, as shown in more detail in FIGS. 5 to 7, each leaflet has a generally shovel-shaped major wall portion 40 which is of generally elliptical configuration with a concave surface 41 on one side and convex surface 42 on the opposite or downstream side. The elliptical wall portion terminates on opposite sides in reversed curved sections which flatten or straighten into lateral edges or skirts 42, the skirts projecting a limited distance in opposite directions to one another. Each skirt 42 terminates in a straight edge 43, and a slide control member 44 protrudes away from the straight edge, the slide control member 44 being somewhat elongated as illustrated in FIG. 5 and having an external curved or convex surface 46 corresponding to the curvature of the bearing surface 34 in its associated channel 28.

Figure 5:
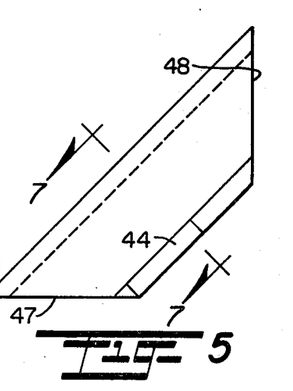
FIG. 5 is a side view of a preferred form of leaflet as illustrated in FIGS. 1 and 2.
Figure 6:
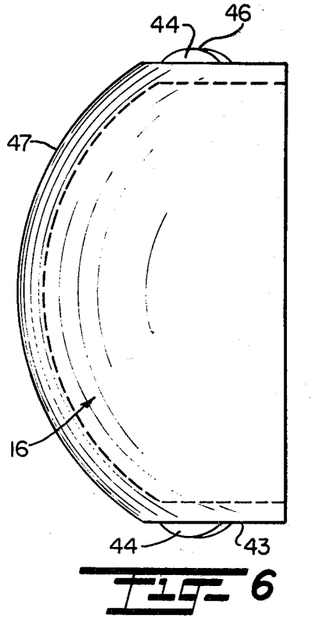
FIG. 6 is a plan view of the leaflet shown in FIG. 5.

As viewed from FIG. 5, each leaflet can be further characterized as being in the essential form of a triangle having a hypotenuse extending centrally of the major wall portion of the leaflet and equilateral side edges 47 and 48 which define the leading or upstream edge of the leaflet and the trailing or downstream edge of the leaflet, respectively. The triangle as described is truncated by the intersection of the sides 47 and 48 with the skirts 42, the skirts 42 extending between the sides 47 and 48 parallel to the hypoteneuse or midsection of the wall portion. Each upstream edge 47, as viewed in FIG. 6, is formed on a radius of curvature corresponding to that of a curved wall section 13 of the annular body and intersects the straight edged skirts 42 at a point corresponding to the straight wall sections 14 of the body. In turn, the downstream edge 48 of each leaflet is movable into flush engagement with a corresponding edge 48 of the opposite leaflet when the leaflets move into the closed position, as illustrated in full in FIG. 2, with the upstream edges 47 movable into contact with the arcuate wall sections 13 of the body.

Considering the relationship between the slide control members 44 and their respective channels 28, it will be noted from FIGS. 1 and 2 that when the leaflets are disposed in their closed position, each slide control member 44 will extend substantially at a 45° angle to the longitudinal axis of the body and parallel to the inner side edge 33 of its associated channel. Each slide control member is of a length corresponding to the length of the longer edges 32 and 33 but is of a width less than the width between the side edges 32 and 33 at their narrowest point along the upstream edge 30. In this way, the slide control member does not have a fixed point of rotation as it advances through the channel but is free to undergo a combination of sliding and pivotal movement as it advances from the closed position to the open position adjacent to or abutting the opposite side edge 32 so as to achieve most effective washing action within the guide channels or pockets 28 as the leaflets are controlled by fluid pressure in their movement between the open and closed positions. Moreover, the slide control members are curved only in a lengthwise direction and are flat across their width so as to correspond to the flat bearing surface of its associated channel and are of a depth to be fully seated within each of the respective channels 28 as illustrated in FIG. 3.

When liquid or fluid under pressure is applied to the upstream or concave surfaces 41 of the leaflets, the opening pressure against the leaflets will cause the slide control members 44 to be advanced from the position shown in full in FIG. 2 to the dotted line position as described. Again, the slide control members will undergo both a sliding or translational movement together with a swinging or pivotal movement through the channels with the upstream end of the slide control member free to slide along the upstream edge 30 and the downstream end of the member being free to advance with respect to the downstream edge 31 of the channel until the member advances from a position abutting the inner side edge 33 to an open position abutting the outer side edge 32. In the open position, the leaflets will have been advanced from a substantially 45° angle to an approximate 5° angle to the longitudinal axis, or just less than parallel to the longitudinal axis. In this relation, the leaflets will have moved in an outward direction toward the inner wall surfaces of the body so as to form an open passageway for the liquid or fluid to flow therethrough and which passageway is free of any obstructions other than the limited projection of the skirts 42 along the straight wall sections. By eliminating any fixed axis or point of rotation between the slide control members and channels, the blood or other liquid flowing therethrough can effectuate more complete washing action of the channels which could otherwise tend to collect the blood or other liquid. Moreover, the blood will be free to pass to a limited extent between the skirt portions 32 and straight wall sections 14 so as to have the effect of a washing action on the mating surfaces between the slide control members 44 and associated channels 28. When the direction of liquid or fluid flow is reversed, the pressure will be shifted to bear against the convex or downstream surface 42 of each leaflet so as to cause the slide control members 44 to undergo reverse movement through the channels in an upstream or radially inward direction until the edges 48 of the leaflets return into closed relation to one another so as to effectively check the flow in the reverse direction. Formation of the slide control members with respect to the pockets 28 in the manner described will eliminate any tendency of the leaflets to move beyond the open position shown in FIG. 2 but at the same time obviates the use of separate limit stops or projections to regulate the degree of opening or closing movement. Still further, the somewhat fan-shaped configuration of the channels 28 in the extension walls along the straight wall sections 14 permits construction of a low profile valve while achieving rapid response time in opening and closing of the valve to reversals in fluid or liquid flow therethrough.

DETAILED DESCRIPTION OF MODIFIED FORM OF INVENTION

In the modified form of invention, a tri-cuspid or tri-leaflet valve is illustrated and generally designated at 50 which is comprised of an annular body 52 provided with extension walls 53 at equally spaced circumferential intervals in which are positioned guide pockets or channels 54 to guide and support occluder leaflets or valve members 55. In the tri-leaflet form, a series of three leaflets are positioned within the body, each being of corresponding size and width having slide control members 56 on opposite sides of each leaflet which are movable through the guide channels 54 between a closed position as illustrated in FIG. 8 and an open position as illustrated in FIG. 10.

The annular body 52 is once again of generally channel-shaped configuration having a straight inner wall surface 58 bounded by flared ends 59 and 60 on its downstream and upstream sides, respectively. A suture ring 62 is positioned within the channel formed by the flared ends 59 and 60 and is provided with a collar 63 projecting in a radial outward direction from the body to facilitate implantation as a mitral valve in the manner described in the preferred form. Although the upstream end 60 of the body is flat, the downstream end 59 is somewhat scalloped or concave, as indicated at 64 in FIG. 9, in its extension between the extension walls 53. The extension walls 53 in turn project in an axial direction away from the main wall of the body and are of somewhat triangular cross-section as viewed in FIG. 8, so as to present radially inwardly inclining, equilateral side surfaces 65 and 66 which intrude for a limited distance from the inner straight wall surface of the body. As a result, the extension walls are formed so as to be of gradually increased thickness in extending in a downstream direction away from the body 52 and terminate in inclined downstream surfaces 67 and 68 which are joined or interconnected by a horizontal edge 69.

Each of the channels 54 is formed in the sides 65 and 66 of each extension wall 53 and correspond in construction as well as intended function with the channels 28 of the preferred form of invention. Accordingly, like parts or surfaces of the channels 54 are correspondingly enumerated to that of the preferred form of FIGS. 1 to 7.

Figure 8:
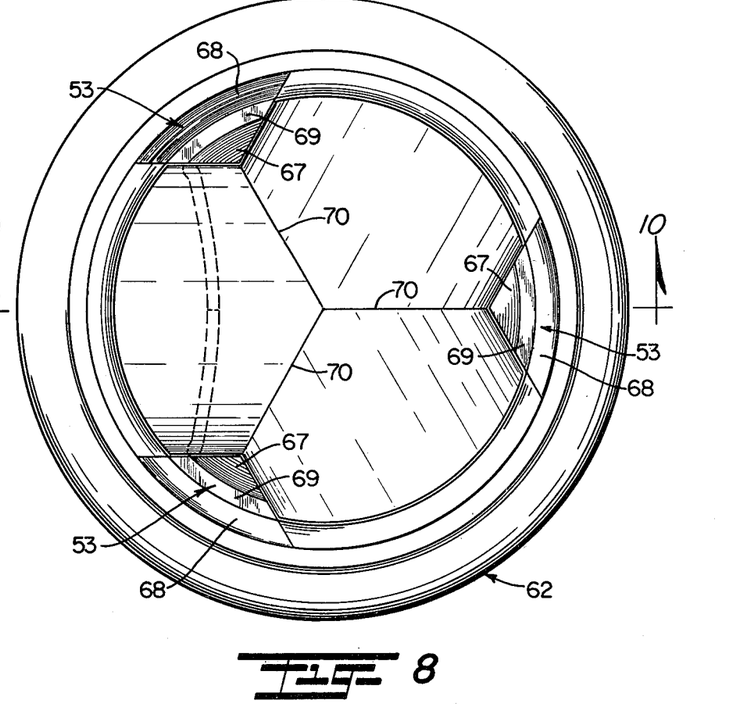
FIG. 8 is a plan view of a modified form of tri-leaflet valve construction with one portion broken away to illustrate the configuration of a channel for guiding movement of the leaflets therein.
Figure 9:
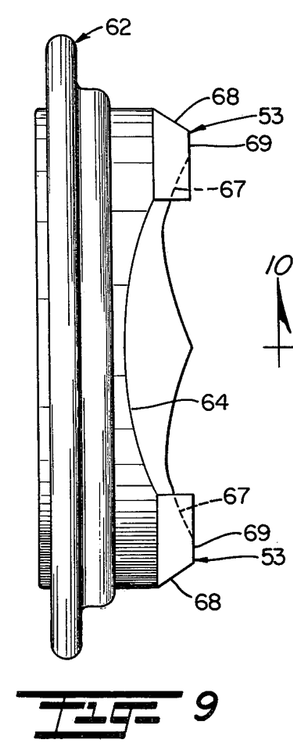
FIG. 9 is a front view of the valve construction shown in FIG. 8.
Figure 10:
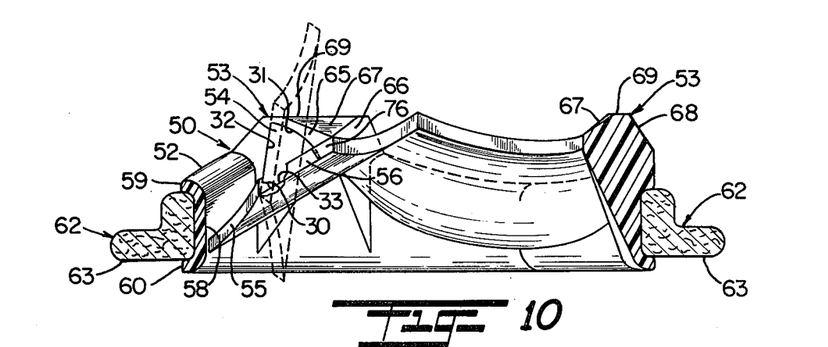
FIG. 10 is a cross-sectional view taken about lines 10—10 of FIG. 8.
Figure 11:
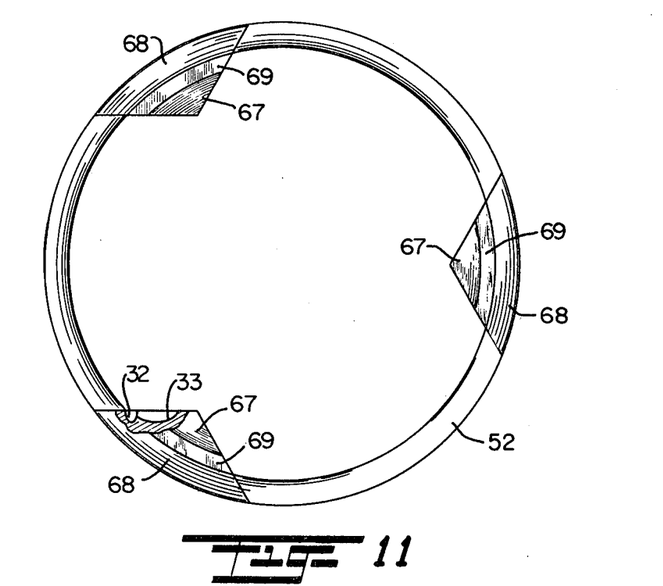
FIG. 11 is a plan view of a modified form of valve body as shown in FIG. 9 with a portion broken away to illustrate the configuration of one of the guide channels.
Figure 12:
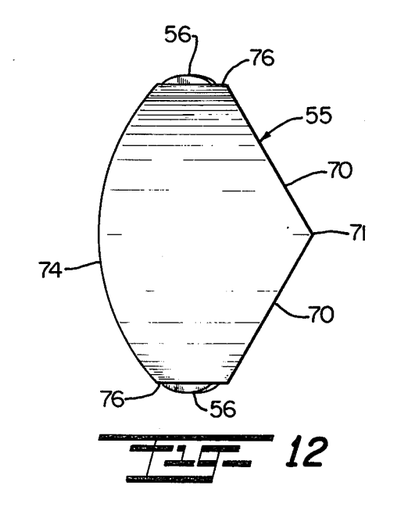
FIG. 12 is a plan view of one of the occluder leaflets of the modified form of invention.
Figure 13:
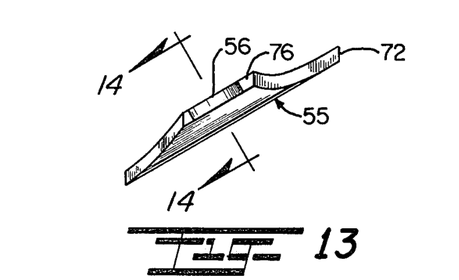
FIG. 13 is a front view of the occluder leaflet shown in FIG. 12.
Figure 14:
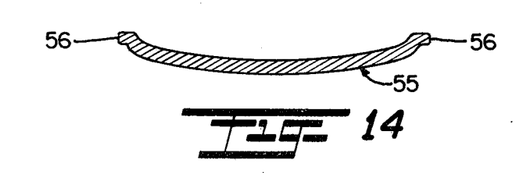
FIG. 14 is a cross-sectional view taken about lines 14—14 of FIG. 13.

As shown in FIGS. 12 to 14, each occluder leaflet or valve member 55 is of corresponding size and configuration and is dimensioned for insertion between confronting sides 65 and 66 of adjacent extension walls so as to move between a closed position as shown in full in FIG. 8 and an open position as shown in dotted form in FIG. 10. Each occluder leaflet can be generally characterized as being shovel-shaped and of a somewhat flatter curved configuration than the preferred form of bi-leaflet arrangement shown in FIGS. 1 to 7. Each leaflet has leading straight edges 70 which converge to an apex or point 71 and are somewhat beveled or tapered as indicated at 72 so as to move into flush engagement with adjoining leading edges of the other leaflets in the closed position shown in FIG. 8. In addition, each leaflet has a beveled trailing edge 74 which is formed on a radius of curvature corresponding to the inner wall surface 58 of the body with opposite ends of the trailing edge 74 intersecting straight lateral edges 76 on opposite sides of each leaflet. A slide control member 56 protrudes from the lateral edge 76 on each side of the leaflet and is of generally lobe-shaped configuration corresponding to the configuration of the slide control members 44 of the preferred form. The lateral edges 76 are of a length so as to be free to slide or advance along the correspondingly flat surfaces of the sides 65 or 66 of the extension walls with the slide control member 56 movable through a guide channel 54 in controlling opening and closing movement of the leaflets.

It will be noted in the tri-leaflet configuration, that the leading edges of the leaflets 55 define a generally Y-shaped parting line in the closed position; and similarly, each pair of adjoining leaflets define a Y-shaped parting line with a common extension wall as seen from a consideration of FIG. 8.

The modified form of valve is characterized by being of a somewhat lower profile than the preferred form and in certain applications, such as, for implantation in place of the aortic valve will better conform to the configuration of the comissures of the natural valves. Moreover, the particular configuration of the valve body enables the leaflets to be positioned somewhat further down into the valve body so as to be of a lower profile than the bi-leaflet valve.

Preferred Form of Single Leaflet Valve

A preferred form of single leaflet valve 80 includes an annular valve body 81 having diametrically opposed, arcuate wall sections 82 interconnected by straight wall sections 84, and a suture ring 15 corresponding to that illustrated in FIG. 1, is mounted in outer surrounding relation to the valve body. A single occluder leaflet 86 is disposed for pivotal movement within the valve body between a closed position, as illustrated in full in FIG. 16, extending at an acute angle to a plane through the valve body and an open position extending at an acute angle to the longitudinal axis of the valve body, as illustrated in dotted form in FIG. 16.

Figures 15, 16, 17, 18:
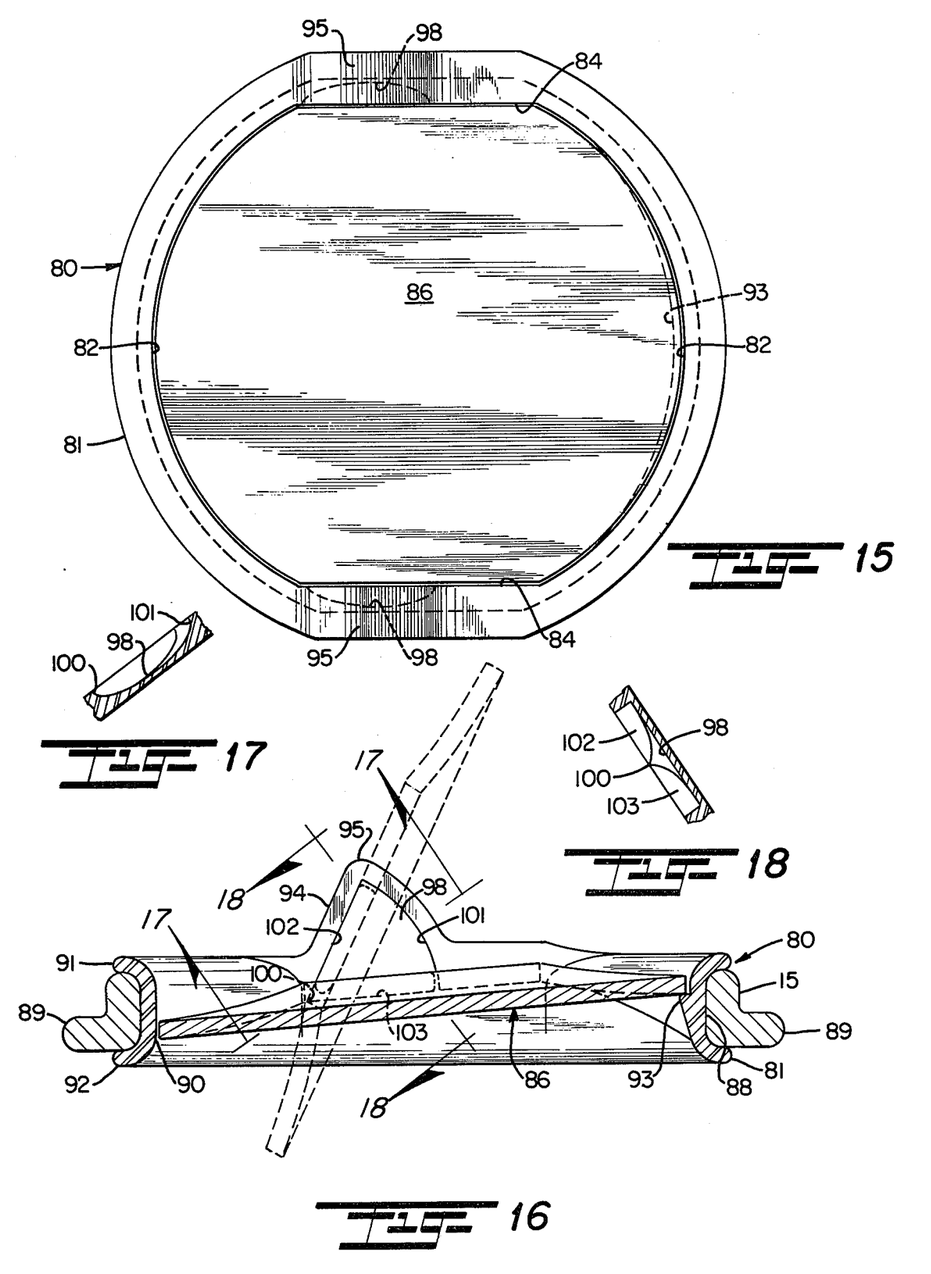
FIG. 15 is a plan view of a preferred form of single leaflet artificial heart valve construction.
FIG. 16 is a cross-sectional view of the valve assembly shown in FIG. 15 and illustrating the mounting of a suture ring thereon.
FIG. 17 is a cross-sectional view taken about lines 17—17 of FIG. 16.
FIG. 18 is a cross-sectional view of a guide pocket taken about lines 18—18 of FIG. 16.

Referring in more detail to the construction of the valve body 81, both the arcuate wall sections 82 and straight wall sections 84 again define a general channel-shaped member having an external concave or channel-shaped external wall surface 88 adapted to receive the suture ring 15, and the ring includes an outwardly projecting collar 89 to facilitate implantation of the valve into the heart, for instance, as a substitute for the mitral valve. Of course, the suture ring may be modified as necessary according to the particular locus of the implantation into the heart. An inner wall surface 90 of the body 81 is characterized by being relatively flat throughout its greater height, save for the downstream and upstream ends 91 and 92 which flare outwardly to form the external wall 88, and an arcuate ledge 93 is formed in the inner wall to extend circumferentially around one of the arcuate wall sections 82, the ledge facing in the downstream direction and adapted to serve as a supporting surface for the leaflet 86 in a manner to be described. In this respect, as shown in FIG. 16, the ledge 93 slopes upwardly from its midpoint, or in other words is given a slight concavity so as to be complementary to the convex upstream surface of the leaflet as hereinafter described. Moreover, each straight wall section 84 has an axial extension 94 which forms a direct axial continuation of the valve body in a downstream direction and terminates in a generally convex or triangular edge 95. Each extension 94 is correspondingly disposed in offset relation to the center line of the valve body so as to extend upwardly from a point relatively near one end of each straight wall section and with the extensions being aligned in opposed confronting relation to one another.

Guide pockets are defined by shallow recesses or bearing surfaces 98, each pocket being of a height to project from a point adjacent to a downstream edge of a wall section 84 to the downstream edge or apex of the axial extension. Each guide pocket 98 is of generally triangular configuration having an upstream end 100 and a curved downstream edge 101 interconnected by divergent side edges 102 and 103. The upstream end 100 is at the intersection of the side edges 102 and 103 or may be truncated somewhat as described with reference to the forms illustrated in FIGS. 1 to 14. In this form, the outer divergent side edge 102 is disposed at an angle on the order of 25° to the longitudinal axis of the valve while the opposite or inner edge 103 is disposed at an angle on the order of 80°–85° to the longitudinal axis. The inner bearing surface 98 of each guide pocket is of generally curvilinear configuration having a generally concave intermediate wall surface which is in the form of a gently curving ellipse in cross-section in a direction between the upstream and downstream edges 100 and 101, but is flat in cross-section at any point in its extension across the width between the divergent edges 102 and 103.

Figure 19:
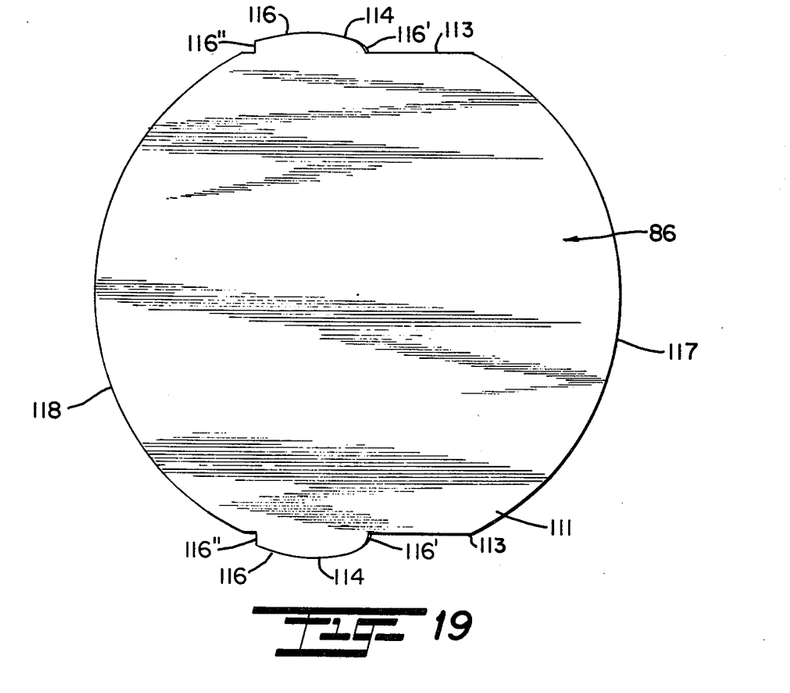
FIG. 19 is a plan view of the single leaflet illustrated in FIGS. 15 and 16.
Figure 20:
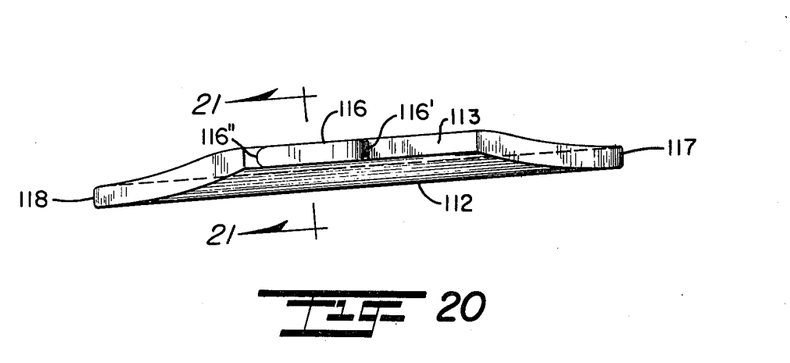
FIG. 20 is a side view of the leaflet shown in FIG. 19.
Figure 21:
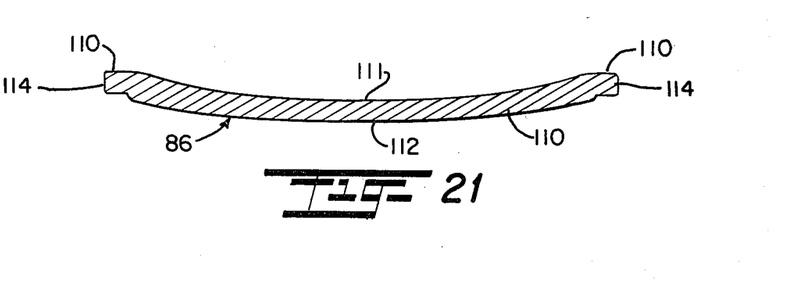
FIG. 21 is a cross-sectional view taken about lines 21—21 of FIG. 20.

The single leaflet 86 is mounted for pivotal movement within the valve body between a closed position as illustrated in full in FIG. 16 and an open position, as shown dotted in FIG. 16. As shown in FIGS. 19 to 21, the leaflet has a generally shovel-shaped major wall portion 110 which is of concavo-convex configuration and provided with a concave surface 111 on its downstream side and a convex surface 112 on its opposite or upstream side. The leaflet terminates on opposite sides in flat side extensions projecting a limited distance in opposite directions to one another so as to terminate in straight edges 113. A guide or slide control member 114 protrudes from each of the straight edges 113 and is somewhat elongated as illustrated in FIG. 19 with a gently curved or convex edge 116 terminating in a squared or juncture with the straight edge 113. The guide member 114 is dimensioned such that when inserted into a respective guide pocket, the edges 116' and 116" will bear slightly against the opposed upstream and downstream edges 100 and 101 with the generally convex edge 116 seated on the bearing surface 98 in the guide pocket. Most desirably, the convex edge 116 is given an elliptical curvature along its length from the leading edge portion 116' rearwardly which corresponds to the elliptical curvature of the bearing surface 98; however, the trailing edge 116" of the convex edge 116 is transversely rounded symmetrically about the center line of the slide member 114 to permit it to pivot smoothly between the open and closed positions and will enable the slide members 114 to move freely into flush engagement with the divergent sides 103 and 104 without interference between the elliptical bearing surface 98 and the convex edge 116. As a result, the guide pockets 98 will establish a precisely controlled angle of the leaflets in the open position and avoid any shifting or misalignment between the trailing edge 116" and upstream edge 100 at the narrow end of the guide pocket.

In the construction of the single leaflet, the lateral edges 113 are dimensioned to correspond substantially to or be slightly less than the length of the straight wall sections 84, and arcuate leading and trailing edge surfaces 117 and 118 correspond substantially to the arcuate wall sections 82 of the valve body, except for allowance of a slight gap between the leading edge 118 and the arcuate wall section 82, as shown in FIGS. 15 and 16. Here, the single leaflet construction can be broadly characterized as being of a gentler slope or curvature than that of the bi-leaflet or tri-leaflet constructions hereinbefore described and is formed on a curvature between the lateral edges on the order of a 6.5° ellipse. Thus, when the guide members 114 are inserted into their respective guide pockets, the leaflet is controlled in its movement between a closed position in which the leading edge 117 engages the arcuate ledge 93 and an open position, again as shown dotted in FIG. 16, in which the leaflet is disposed more nearly parallel to the longitudinal axis of the valve body. By virtue of the slight angle or inclination of the leaflet 86 in the closed position, the leaflet 93 slopes at a corresponding angle radially inwardly and in an upstream direction so that the leading edge 117 will advance into substantially flush relation to the ledge 93. However, owing to the gap formed between the leaflet and arcuate wall section 82 adjacent to the ledge 93 a controlled leakage of blood past the leaflet is permitted in the closed position just sufficient to keep the blood agitated and avoid any tendency to clot or coagulate.

When blood flows under pressure into the heart and is applied to the upstream or convex surface 112 of the leaflet, the opening pressure against the leaflet will cause its slide control members 114 to undergo a combination of sliding and pivotal movement from the position shown in full in FIG. 16 to the dotted line position. In undergoing both a limited sliding or translational movement along with a pivotal movement through the guide pockets, the slide control members 114 will advance from a position abutting the divergent edge 103 to an open position abutting the edge 102. In moving to the open position, the leaflet will have undergone a movement of substantially 60° toward the arcuate wall section of the valve body so as to form open passageways for the blood to flow both along the major and minor orifices and which passageways are free of any obstructions along opposed surfaces of the leaflets. Once again, by eliminating a fixed axis or point of rotation between the guide members and guide pockets, the blood or other liquid flowing therethrough can effectuate more complete washing action of the guide pockets while being free to pass to some extent between the side extensions and straight wall sections, thereby having the effect of a washing action on the mating surfaces between the slide control members 114 and guide pockets 98. When the direction of flow of blood is reversed, the fluid pressure will be applied to the concave surface 111 of each leaflet so as to cause the guide members 114 to undergo reverse movement through the guide pockets in an upstream direction until the leading edge of the leaflet returns into closed relation to the supporting ledge 93 and effectively checks the flow of blood in a reverse direction.

It is therefore to be understood that while preferred and modified form of the invention have been set forth and disclosed herein that various modifications and changes may be made without departing from the spirit and scope of the invention as defined by the appended claims.

We claim:

1. In an artificial heart valve wherein at least one occluder leaflet is disposed for swinging movement within a generally annular valve body, said leaflet having opposed leading and trailing edge surfaces, and a pair of axially directed extensions are disposed at spaced circumferential intervals on said valve body and extend in a downstream direction from said valve body, each extension including a shallow recess having opposed sidewalls diverging away from one another in a downstream direction, the improvement comprising:

said occluder leaflet having a major wall portion of generally elliptical configuration terminating on opposite sides in flat portions extending in opposite directions to one another and normal to said axially directed extensions, said flat portions provided with lateral edge surfaces defining opposite lateral margins of said leaflet, guide means mounting said leaflet for movement between a closed position extending across the central opening in said valve body and an open position extending substantially parallel to and relatively near said valve body and spaced away from the axis of said valve body, said guide means defined by lateral projections disposed on opposed lateral edge surfaces of said leaflet, said lateral projections aligned with and inserted into said recesses on said extensions, each lateral projection being of a width less than the space between said sidewalls, each pair of lateral projections for a leaflet being operative to control combined pivotal and translatory movement of said leaflet between said open and closed positions.

2. In an artificial heart valve according to claim 1, said valve body having an inner wall surface provided with a supporting ledge and the leading edge of said leaflet movable into contact with said supporting ledge in the closed position.

3. In an artificial heart valve according to claim 2, said major wall portion being of concavo-convex configuration with its convex surface on the upstream side and having curved leading and trailing edge surfaces substantially corresponding to the curvature of the inner wall surface of said annular valve body.

4. In an artificial heart valve according to claim 3, said supporting ledge extending circumferentially of said inner wall surfaces for a distance corresponding to said leading edge surface and having a concave surface complementary to the convex surface of said leaflet.

5. In an artificial heart valve according to claim 1, said lateral projections being of narrow, elongated configuration and having gently curved external surfaces substantially along their length, said recesses provided with curved bearing surfaces complementary to the external surfaces of said lateral projections.

6. In an artificial heart valve according to claim 1, the included angle between opposed sidewalls of each recess being on the order of 40°.

7. In an artificial heart valve according to claim 1, each recess being of generally trapezoidal configuration having opposite sidewalls diverging in a downstream direction and each recess having a bearing surface which is concave in cross-section between upstream and downstream edges but is flat in cross-section between opposite sidewalls.

8. In a prosthetic heart valve in which an annular valve body has an inner wall surface interrupted by diametrically opposed, straight wall sections, axially directed extensions are disposed in opposed relation to one another and in offset relation to the axis of said valve body and extend in a downstream direction from said straight wall sections of said body, each extension including a shallow recess of generally trapezoidal configuration having opposed sidewalls diverging in a downstream direction, the improvement comprising:

an occluder leaflet disposed within said valve body and of a size corresponding substantially to the opening in said valve body having a major wall portion of generally elliptical configuration terminating on opposite sides in flat portions extending in opposite directions to one another and normal to said axial extensions, said flat portions provided with lateral edge surfaces defining opposite lateral margins of said leaflet, said leaflet having leading and trailing edge surfaces converging into said lateral edge surfaces, each lateral edge surface extending parallel to and coextensive with one of said straight wall sections and each having a lateral projection inserted into a recess in one of said axial extensions, each said lateral projection being of a length corresponding to the length of a sidewall of said recess and of a width less than the space between said sidewalls, each pair of lateral projections defining guide means operative to control movement of said leaflet between an open position in which said leaflet is movable away from the axis of said valve body into a position substantially parallel to said valve body and a closed position in which said leaflet is disposed for extension angularly across said valve body.

9. In a prosthetic heart valve according to claim 8, said inner wall surface of said valve body provided with a curved supporting ledge portion to support said leaflet in the closed position.

10. In a prosthetic heart valve according to claim 9, each recess provided with an inner concave bearing surface curving in a direction parallel to opposite sidewalls of said recess, and each lateral projection having an external convex edge complementary to the bearing surface of its respective recess, each said convex edge terminating in a transversely rounded straight edge at the upstream end thereof.

11. In a heart valve according to claim 10, each said lateral projection being elongated with the convex edge of each lateral projection terminating in said transversely rounded straight edge at one end and a rounded edge at the opposite end thereof.

12. In a heart valve according to claim 10, said transversely rounded straight edge being contiguous to the pivotal axis of said leaflet.

13. In a heart valve according to claim 10, said bearing surface having an elliptical curvature, said convex edge of each said lateral projection being elongated with an elliptical surface portion complementary to the elliptical curvature of said bearing surface.

14. In a heart valve according to claim 8, each said recess being in the form of a guide pocket having divergent side edges defining limits to the movement of each respective lateral projection between the open and closed positions of said leaflet.

15. In a heart valve according to claim 8, each said generally trapezoidal recess having a relatively narrow upstream edge and a relatively wide downstream edge, the transverse width of each said lateral projection being less than the width of said upstream edge of each said respective recess.

16. In an artificial heart valve wherein a plurality of occluder leaflets are disposed for pivotal swinging movement within a generally annular valve body, each leaflet having opposed lateral edge surfaces and leading and trailing edge surfaces, the improvement comprising:
a plurality of axially directed extensions disposed at spaced circumferential intervals around the inner wall surface of said body and offset from the central axis of said valve body, each extension having radially inwardly directed convergent wall surfaces including a shallow recess of generally polygonal configuration in each convergent wall surface and opposed sidewalls in each recess diverging away from one another in a downstream direction, each recess having a bearing surface which is concave in cross-section between upstream and downstream edges but is flat in cross-section between opposite sidewalls, and
said occluder leaflets disposed within said valve body including guide means mounting said leaflets for movement between a closed position extending across the central opening in said valve body at an acute angle to the longitudinal axis of said body and an open position extending substantially parallel to the axis of said valve body, each leaflet being of concavo-convex configuration between said opposed lateral edge surfaces, said guide means defined by lateral projections on said opposed lateral edge surfaces of each leaflet, said lateral projections insertable into aligned ones of said recesses on said extensions, each pair of lateral projections for a leaflet being operative to control movement of said leaflet between said open and closed position.

17. In an artificial heart valve according to claim 16, said leaflets being of curved configuration and having curved leading edge surfaces substantially corresponding to the curvature of the inner wall surface of said annular valve body along an area of contact therewith.

18. In an artificial heart valve according to claim 16, said lateral projections being of narrow, elongated configuration and having external surfaces curved along their length.

19. In an artificial heart valve according to claim 18, the curvature of said lateral projections corresponding to the curvature of the inner wall surfaces of said respective recesses, one of said opposed sidewalls being disposed at an angle of 5° to 9° with respect to the longitudinal axis of said valve, and the other of said opposed sidewalls being disposed at an angle of substantially 45° with respect to said longitudinal axis.

20. In an artificial heart valve according to claim 19, each recess being of generally trapezoidal configuration having an edge surface interconnecting opposed sidewalls on the upstream side wider than that of said lateral projections.

21. A prosthetic heart valve comprising:
an annular valve body having axially directed extensions at spaced intervals and extending in a downstream direction from an inner wall surface of said body, each said extension having flat wall sections intruding from the inner wall of said body and inclined radially inwardly with respect to said inner wall surface of said annular valve body, each wall section including a shallow recess of generally trapezoidal configuration having opposed sidewalls diverging in a downstream direction, each recess having a bearing surface which is concave in cross-section between upstream and downstream edges but is flat in cross-section between opposite sidewalls; and
a plurality of occluder leaflets disposed within said valve body, each leaflet having leading and trailing edge surfaces converging into opposed lateral edge surfaces, each lateral edge surface having a lateral projection insertable into a recess in one of said extensions, each projection being of a length corresponding to the length of a sidewall of said recess and of a width less than the space between said sidewalls, each pair of lateral projections defining guide means for its respective leaflet operative to control combined pivotal and translatory movement of said leaflet from a closed position in which said leaflets are disposed for extension angularly across said valve body with said trailing edge surfaces of said leaflets in abutting relation to one another and to undergo outward pivotal and translatory movement away form the axis of said valve body to an open position in which said leaflet is disposed substantially parallel to said valve body.

22. In a prosthetic heart valve according to claim 21, each lateral projection having an external convex surface engageable with the bearing surface of said respective recess.

23. In a prosthetic heart valve comprising:
an annular valve body having axially directed extensions at spaced intervals and extending in a downstream direction from an inner wall surface of said body, each extension including a shallow recess of generally trapezoidal configuration having opposed sidewalls diverging in a downstream direction, each recess having a bearing surface which is concave in cross-section between upstream and downstream edges but is flat in cross-section between opposite sidewalls; and
a plurality of occluder leaflets disposed within said valve body, each leaflet being curved across its substantial width and provided with leading and trailing edge surfaces converging into opposed flat lateral edge surfaces extending normal to said axially directed extensions, each lateral edge surface having a lateral projection insertable into a recess in one of said extensions, each projection being of a length corresponding to the length of a sidewall of said recess and of a width less than the space between said sidewalls, each pair of lateral projections defining guide means for their respective leaflet operative to control combined pivotal and translatory movement of said leaflet from a closed position in which said leaflets are disposed for extension angularly across said valve body with said trailing edge surfaces of said leaflets in abutting relation to one another and to undergo outward pivotal and translatory movement away from the axis of said valve body to an open position in which said leaflet is disposed substantially parallel to said valve body.

* * * * *

UNITED STATES PATENT AND TRADEMARK OFFICE
CERTIFICATE OF CORRECTION

PATENT NO. : 4,446,577
DATED : May 8, 1984
INVENTOR(S) : Louis C. Meyer and Samuel H. Goodenough It is certified that error appears in the above—identified patent and that said Letters Patent is hereby corrected as shown below:

In the Specification:

Column 4, line 57, cancel "18.
Column 9, line 56, after "or" insert -- straight edge 116'' and a rounded edge 116' at its --.
Column 10, line 3, cancel "103 and 104" and substitute -- 102 and 103 --.
Column 10, line 32, cancel "leaflet" and substitute -- ledge --.
Column 11, line 7, cancel "form" and substitute -- forms --.

In the Claims:

Column 14, line 28 (Claim 21), cancel "form" and substitute -- from --.
Column 14, line 57 (Claim 23), cancel "their" and substitute -- its --.

Signed and Sealed this

Twenty-second Day of January 1985

[SEAL]

Attest:

DONALD J. QUIGG

*Attesting Officer*   *Acting Commissioner of Patents and Trademarks*